(12) United States Patent
Costantino et al.

(10) Patent No.: US 7,585,971 B2
(45) Date of Patent: Sep. 8, 2009

(54) PROCESS FOR THE PREPARATION OF DROSPIRENONE

(75) Inventors: Francesca Costantino, Milan (IT); Roberto Lenna, S. Giorgio Su Legnano (IT); Silvia Piuri, Saronno (IT)

(73) Assignee: Industriale Chimica S.R.L., Milan (IT)

( * ) Notice: Subject to any disclaimer, the term of this patent is extended or adjusted under 35 U.S.C. 154(b) by 937 days.

(21) Appl. No.: 11/067,769

(22) Filed: Feb. 28, 2005

(65) Prior Publication Data

US 2005/0192450 A1   Sep. 1, 2005

(30) Foreign Application Priority Data

Mar. 1, 2004   (IT)   .......................... MI2004A0367

(51) Int. Cl.
*C07J 53/00*   (2006.01)
(52) U.S. Cl. ........................................................ 540/15
(58) Field of Classification Search .................... 540/15
See application file for complete search history.

(56) References Cited

U.S. PATENT DOCUMENTS 4,559,331 A * 12/1985 Nickisch et al. ............. 514/173

FOREIGN PATENT DOCUMENTS

| CA | 2498634 | 9/2005 |
| EP | 0075189 A1 * | 3/1983 |
| EP | 1571153 | 9/2005 |

* cited by examiner

*Primary Examiner*—Barbara P Badio
(74) *Attorney, Agent, or Firm*—Stetina Brunda Garred & Brucker

(57) ABSTRACT

A process is described for preparing drospirenone, a synthetic steroid with progestogenic, antimineralocorticoid and antiandrogenic activity, useful for the preparation of pharmaceutical compositions with contraceptive action, starting from 5,6β-epoxy-7β-hydroxy-15β,16β-methylene-3β-pivaloyloxy-5β-androstan-17-one.

35 Claims, No Drawings

PROCESS FOR THE PREPARATION OF DROSPIRENONE

FIELD OF THE INVENTION

The present invention relates to the field of processes for synthesising steroids, and in particular to a process for the industrial-scale preparation of drospirenone.

STATE OF THE ART

The compound of formula (I) given hereinafter, whose chemical name is 6β,7β; 15β,16β-dimethylene-3-oxo-17α-pregn-4-ene-21,17-carbolactone, is commonly known as drospirenone:

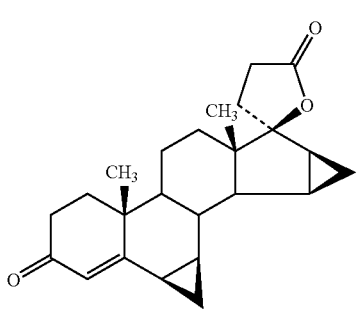

(I)

It is a synthetic steroid with progestogenic, antimineralocorticoid and antiandrogenic activity; by virtue of these characteristics drospirenone has long been used for preparing pharmaceutical compositions with contraceptive action for oral administration.

Many processes are known in the literature for preparing drospirenone, for example the process described in European Patent No. 0 075 189, starting from 3β,7α,15α-trihydroxy-5-androsten-17-one passing via the intermediate 5,6β-epoxy-7β-hydroxy-15β,16β-methylene-3β-pivaloyloxy-5β-androstan-17-one.

As described in EP 0 075 189, this intermediate is then transformed into 7α-chloro-5,6β-epoxy-15β,16β-methylene-3β-pivaloyloxy-5β-androstan-17-one with a reaction that proposes the use of tetrachloromethane both as reagent and as reaction solvent. The use of this, highly toxic, solvent in relatively large quantities, constitutes one of the unfavourable aspects of this process.

In the process described in EP 0 075 189, from the intermediate 7α-chloro-5,6β-epoxy-15β,16β-methylene-3β-pivaloyloxy-5β-androstan-17-one, via several passages, the intermediate 17α-(3-hydroxypropyl)-6β,7β; 15β,16β-dimethylene-5β-androstan-3β,5,17β-triol is arrived at, from which the final product drospirenone is obtained by oxidation with a pyridine/water/chromic anhydride mixture under hot conditions. This passage constitutes a further disadvantage of the known process: chromic anhydride, as all Cr(VI) compounds, is actually a known carcinogen whose use is subject to legislative restrictions such that the precautions required during the use and disposal of these products, render them practically unusable. Moreover, the formation of drospirenone in an acid environment unavoidably generates a range of impurities, as was highlighted in European Patent No. 0 918 791 and in *Tetrahedron Letters* 27(45), 5463-5466, 1986.

The need was therefore felt for a process that enables high purity drospirenone to be prepared, without however presenting the aforesaid disadvantages of processes of the known art.

SUMMARY OF THE INVENTION

The Applicant has now found a new process to enable drospirenone with a high degree of purity to be obtained, suitable for use for the preparation of pharmaceutical compositions, which overcomes the disadvantages highlighted above related to the use of toxic and carcinogenic reagents and to the formation of many impurities in the final step of drospirenone formation.

Subject of the present invention is therefore a process for the preparation of drospirenone, comprising the following steps:

a) bromination of 5,6β-epoxy-7β-hydroxy-15β,16β-methylene-3β-pivaloyloxy-5β-androstan-17-one of formula (II), in position 7α, to obtain 7α-bromo-5,6β-epoxy-15β,16β-methylene-3β-pivaloyloxy-5β-androstan-17-one of formula (III)

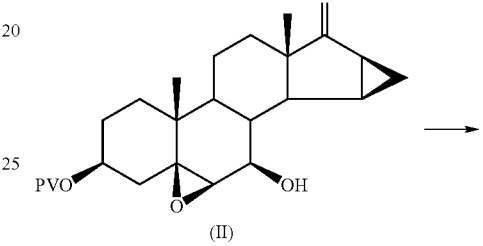

b) opening the epoxy ring of, and removing bromine from, 7α-bromo-5,6β-epoxy-15β,16β-methylene-3β-pivaloyloxy-5β-androstan-17-one of formula (III) to obtain 5-hydroxy-15β,16β-methylene-3β-pivaloyloxy-5β-androst-6-en-17-one of formula (IV)

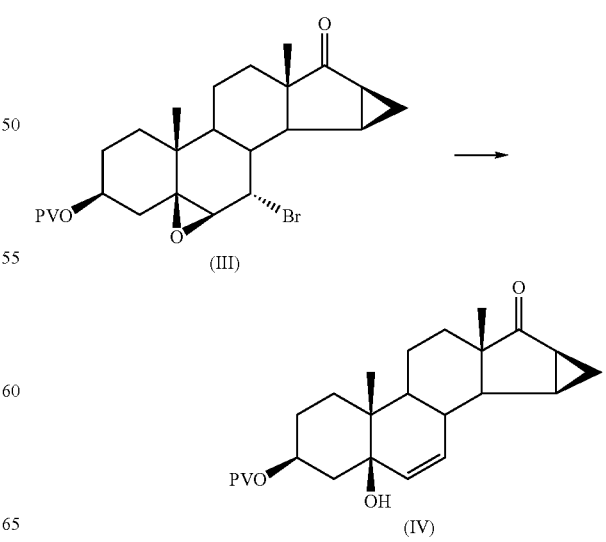

c) hydrolysis of the pivaloyl group of 5-hydroxy-15β,16β-methylene-3β-pivaloyloxy-5β-androst-6-en-17-one of formula (IV) to obtain 3β,5-dihydroxy-15β,16β-methylene-5β-androst-6-en-17-one of formula (V)

e) reacting 3β,5-dihydroxy-6β,7β;15β,16β-dimethylene-5β-androst-17-one of formula (VI) with propargyl alcohol to obtain 17α-(3-hydroxy-1-propinyl)-6β,7β;15β,16β-dimethylene-5β-androstan-3β,5,17β-triol of formula (VII)

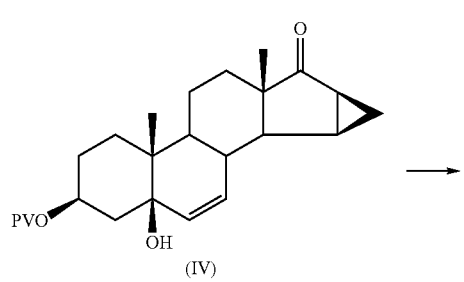

(IV)

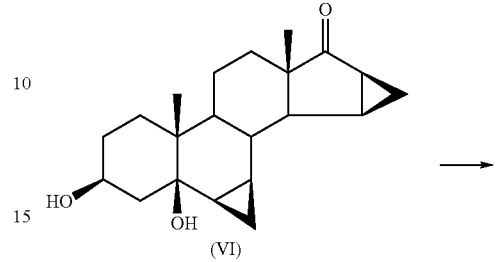

(VI)

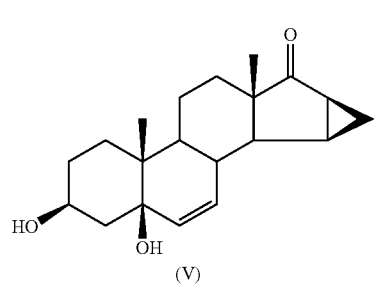

(V)

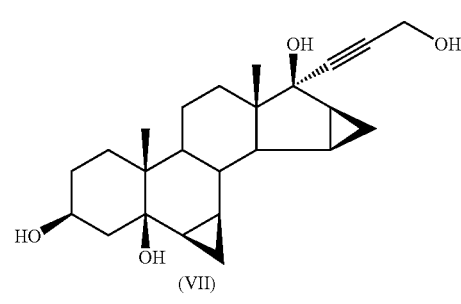

(VII)

d) methylenation of 3β, 5-dihydroxy-15β,16β-methylene-5β-androst-6-en-17-one of formula (V), at the Δ⁶ double bond, to obtain 3β,5-dihydroxy-6β,7β;15β,16β-dimethylene-5β-androst-17-one of formula (VI)

f) hydrogenating 17α-(3-hydroxy-1-propinyl)-6β,7β;15β,16β-dimethylene-5β-androstan-3β,5,17β-triol of formula (VII) to obtain 17 α-(3-hydroxypropyl)-6β,7β;15β,16β-dimethylene-5β-androstan-3β,5,17β-triol of formula (VIII)

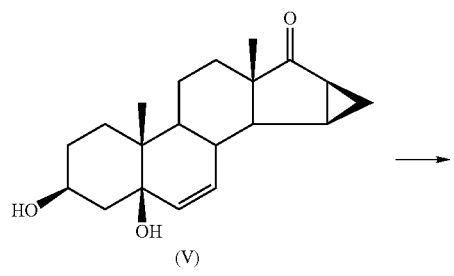

(V)

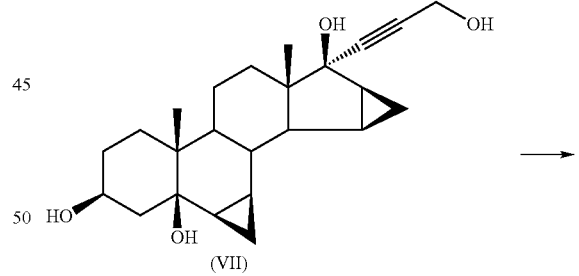

(VII)

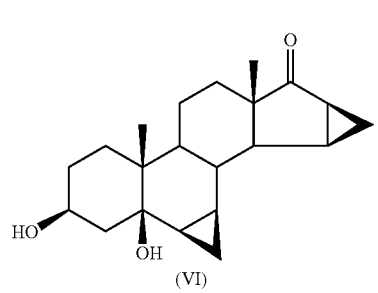

(VI)

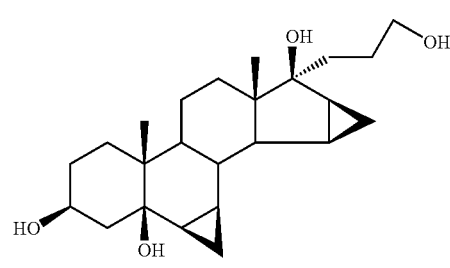

(VIII)

g) oxidising 17α-(3-hydroxypropyl)-6β,7β;15β,16β-dimethylene-5β-androstan-3β,5,17β-triol of formula (VIII) to obtain drospirenone of formula (I)

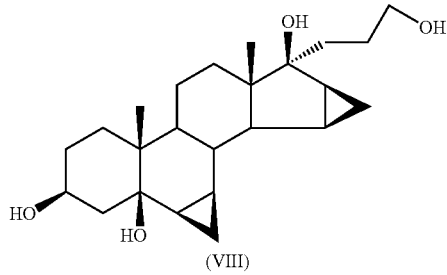

(VIII)

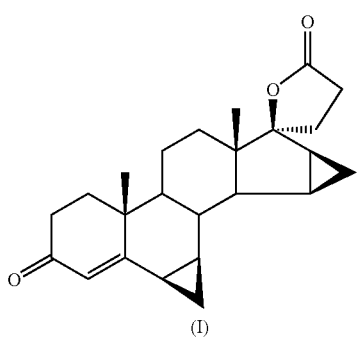

(I)

said process being characterised in that:
i) the 5,6β-epoxy-7β-hydroxy-15β,16β-methylene-3β-pivaloyloxy-5β-androstan-17-one of formula (II) in step a) is reacted with mesyl chloride to obtain the corresponding mesylate of formula (II-Ms), which is not isolated and from which 7α-bromo-5,6β-epoxy-15β,16β-methylene-3β-pivaloyloxy-5β-androstan-17-one of formula (III) is obtained by adding lithium bromide

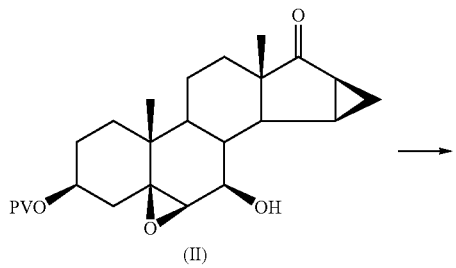

(II)

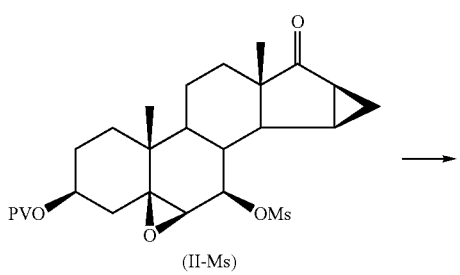

(II-Ms)

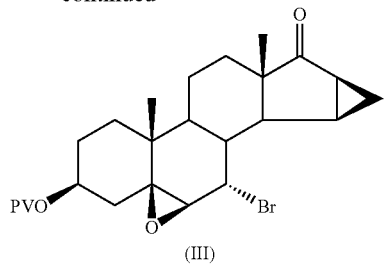

(III)

and
ii) said oxidation in step g) is carried out under such conditions that drospirenone forms under non-acidic pH conditions.

Further subjects of the invention are the following intermediates 6β,7β;15β,16β-dimethylene-5β-hydroxy-3-oxo-17α-pregn-21,17-carbolactol and 6β,7β;15β,16β-dimethylene-3-oxo-17α-pregn-4-en-21,17-carbolactol of formula (X), in the form of an isomeric mixture:

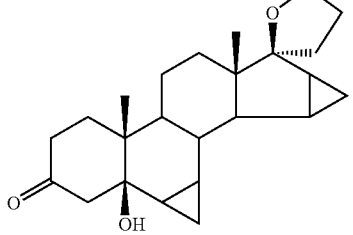

(IX)

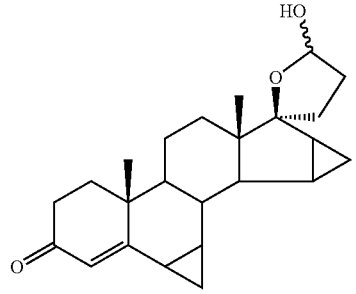

(X)

Characteristics and advantages of the invention will be illustrated in detail in the description that follows.

DETAILED DESCRIPTION OF THE INVENTION

The starting compound of the present process, i.e. 5,6β-epoxy-7β-hydroxy-15β,16β-methylene-3β-pivaloyloxy-5β-androstan-17-one, can be easily obtained from commercially available products in accordance with processes well known to those skilled of the art, for example from 3β-hydroxy-5-androsten-17-one as described in European Patent No. 0 075 189.

According to a preferred embodiment of the present process, the bromination reaction of step a) is achieved by adding mesyl chloride and pyridine to the starting compound at room temperature with the formation of the corresponding mesylate, then adding lithium bromide dissolved in water and bringing the temperature to values ranging from 70 to 75° C.

At step g) of the present process, 17α-(3-hydroxypropyl)-6β,7β;15β,16β-dimethylene-5β-androstan-3β,5,17β-triol is oxidised to drospirenone directly, or by passing via the intermediate, 6β,7β;15β,16β-dimethylene-5β-hydroxy-3-oxo-17α-pregn-21,17-carbolactol, which can in turn be oxidised to drospirenone directly or by passing via an intermediate, 6β,7β;15β,16β-dimethylene-3-oxo-17α-pregn-4-en-21,17-carbolactol, which is then oxidised to drospirenone.

According to the present process, 17α-(3-hydroxypropyl)-6β,7β;15β,16β-dimethylene-5β-androstan-3β,5,17β-triol can be oxidised to drospirenone directly by reaction with manganese oxide in toluene at a temperature between 40 and 110° C.; or by reaction with a base chosen from aluminium isopropylate, potassium tert-butylate and sodium methylate in an organic solvent chosen from toluene and xylene, in the presence of a ketone selected from methylisobutylketone, acetone and cyclohexanone, at a temperature between 80 and 110° C.

When the oxidation reaction of 17α-(3-hydroxypropyl)-6β,7β;15β,16β-dimethylene-5β-androstan-3β,5,17β-triol to drospirenone passes via 6β,7β;15β,16β-dimethylene-5β-hydroxy-3-oxo-17α-pregn-21,17-carbolactol, this latter is prepared in the form of an isomeric mixture by reacting the aforesaid triol with a reagent selected from oxalyl chloride and pyridine-$SO_3$ in an organic solvent selected from dimethylsulfoxide and a dimethylsulfoxide-methylene chloride mixture, in the presence of triethylamine. The intermediate 6β,7β;15β,16β-dimethylene-5β-hydroxy-3-oxo-17α-pregn-21,17-carbolactol, having been obtained in this manner in the form of an isomeric mixture, can then be subjected to oxidation to obtain drospirenone, for example by reaction with manganese dioxide in toluene at a temperature between 40 and 110° C.; or by reaction with a base selected from aluminium isopropylate, potassium tert-butylate and methylated sodium in an organic solvent selected from toluene and xylene, in the presence of a ketone selected from methylisobutylketone, acetone and cyclohexanone, at a temperature between 80 and 110° C.

According to a further embodiment of the present process, oxidation of 6β,7β;15β,16β-dimethylene-5β-hydroxy-3-oxo-17-pregn-21,17-carbolactol to drospirenone is carried out by reaction with sodium hypochlorite or calcium hypochlorite in an organic solvent selected from ethyl acetate, acetonitrile, toluene and methylene chloride at a temperature between 0 and 110° C. in the presence of an organic base selected from pyridine, 1,8-diazabicyclo[5.4.0]undec-7-ene and 1,5-diazabicyclo[4.3.0]non-5-ene, in the presence of a basic aqueous solution, and in the presence of a reagent selected from the 4-methoxy-2,2,6,6-tetramethylpiperidine-1-oxyl radical, the 4-(benzoyloxy)-2,2,6,6-tetramethylpiperidine-1-oxyl radical, the 4-hydroxy-2,2,6,6-tetramethylpiperidine-1-oxyl radical and the 2,2,6,6-tetramethylpiperidine-1-oxyl radical, said reaction being followed by distillation of the organic solvent.

According to the present process, oxidation of 6β,7β;15β,16β-dimethylene-5β-hydroxy-3-oxo-17α-pregn-21,17-carbolactol to drospirenone can be undertaken directly as said above, or by passing via the intermediate 6β,7β;15β,16β-dimethylene-3-oxo-17α-pregn-4-en-21,17-carbolactol; in this latter case, 6β,7β;15β,16β-dimethylene-5β-hydroxy-3-oxo-17α-pregn-21,17-carbolactol prepared in the form of an isomeric mixture as described above is reacted with a reagent selected from sodium methylate in methanol, potassium tert-butylate in tert-butanol, pyridine and a mixture of water and pyridine, at a temperature between 15 and 65° C. to obtain 6β,7β;15β,16β-dimethylene-3-oxo-17α-pregn-4-en-21,17-carbolactol in the form of an isomeric mixture, which is then subjected to oxidation to obtain drospirenone.

Oxidation of 6β,7β;15β,16β-dimethylene-3-oxo-17α-pregn-4-en-21,17-carbolactol to drospirenone can be carried out for example with manganese dioxide in toluene at a temperature between 40 and 110° C.; or with a base selected from aluminium isopropylate, potassium tert-butylate and sodium methylate in an organic solvent selected from toluene and xylene, in the presence of a ketone selected from methylisobutylketone, acetone and cyclohexanone, at a temperature between 80 and 110° C.

According to a further embodiment of the present invention, said oxidation of 6β,7β;15β,16β-dimethylene-3-oxo-17α-pregn-4-en-21,17-carbolactol in the form of an isomeric mixture to drospirenone is carried out by reaction with sodium hypochlorite or calcium hypochlorite in an organic solvent selected from ethyl acetate, acetonitrile, toluene and methylene chloride, at a temperature between 0 and 110° C., in the presence of an organic base selected from pyridine, 1,8-diazabicyclo[5.4.0]undec-7-ene and 1,5-diazabicyclo[4.3.0]non-5-ene, in the presence of a basic aqueous solution, and in the presence of a reagent selected from the 4-methoxy-2,2,6,6-tetramethylpiperidine-1-oxyl radical, the 4-(benzoyloxy)-2,2,6,6-tetramethylpiperidine-1-oxyl radical, the 4-hydroxy-2,2,6,6-tetramethylpiperidine-1-oxyl radical and the 2,2,6,6-tetramethylpiperidine-1-oxyl radical, said reaction being followed by distillation of the organic solvent. Preferably this oxidation of 6β,7β;15β,16β-dimethylene-3-oxo-17α-pregn-4-en-21,17-carbolactol to drospirenone is carried out by reaction with calcium hypochlorite in methylene chloride at a temperature between 0 and 20° C. in the presence of the 2,2,6,6-tetramethylpiperidine-1-oxyl radical and in the presence of an aqueous sodium bicarbonate solution.

According to a further embodiment of the present process, said oxidation of 6β,7β;15β,16β-dimethylene-3-oxo-17α-pregn-4-en-21,17-carbolactol in the form of an isomeric mixture to drospirenone is carried out by reaction with a ruthenium salt in the presence of a base and a drying agent in an organic solvent selected from ethyl acetate, acetonitrile, toluene and methylene chloride, at a temperature between 0 and 110° C. Preferably, said oxidation reaction is carried out at a temperature between 15 and 30° C. by reaction with tetrapropylammonium perruthenate, using N-methylmorpholine N-oxide as the base, molecular sieves as drying agent and acetonitrile as organic solvent.

According to a further embodiment of the present process, this oxidation reaction of 6β,7β;15β,16β-dimethylene-3-oxo-17α-pregn-4-en-21,17-carbolactol in form of isomeric mixture to drospirenone is carried out by microbiological route using acetic bacteria, preferably belonging to the strain classified as *Acetobacter aceti* MIM ANTO.

The bio-transformation occurs with analogous yields by adding the 6β,7β;15β,16β-dimethylene-3-oxo-17α-pregn-4-en-21,17-carbolactol in form of isomeric mixture both to the brothculture 24 hours after inoculum, and to the bacterial cells obtained following to centrifugation of the same brothculture and re-suspended in phosphate buffer at pH=6.

When the brothculture is used, it is typically used the culture of cells submerged in a flask in a suitable culture medium for a growth time of 24 hours after inoculum at 28° C. As the culture medium it is preferably used a culture medium called GLY, composed of glycerol (25 g/l) and yeast extract (10 g/l) and distilled water, brought to pH=5. The culture medium may be sterilised at 115° C. for 20 minutes at a pressure of 0.75 atm.

According to a preferred embodiment of the present microbiological oxidation, the above said carbolactol in the form of isomeric mixture is added so that its concentration in the brothculture, or in the suspension of the cells obtained by centrifugation of the brothculture, is equal to 2 g/l.

The drospirenone obtained with the present process as described above, has a high degree of purity which could be still increased by subjecting the crude product coming from the oxidation in step g) to a purification process, comprising gel chromatography with an organic solvent as eluent, possibly followed by crystallisation.

The gel used according to the invention can be selected from the group consisting of silica gel, alumina, Magnesium silicate (for example that marketed as Florisil®), and dextran (for example that marketed as Sephadex®), and can have a particle size distribution ranging from 5 to 200 μm, while the eluent can for example be selected from the group consisting of ethyl ether, isopropyl ether, ethyl acetate, isopropyl acetate, methylene chloride, acetone, tetrahydrofuran, methanol, ethanol, isopropanol, hexane (n-hexane or mixture of isomers), heptane (n-heptane or a mixture of isomers) and their mixtures. Preferably the gel is silica gel and the eluent is ethyl ether.

The weight ratio gel to drospirenone can be comprised for example between 5:1 and 25:1. Preferably, the weight ratio gel to drospirenone is equal to 10:1 and the eluent is pure ethyl ether.

The drospirenone to be purified can be loaded after absorption onto dry gel or dissolved in the elution solvent.

Column preparation and elution are preferably carried out at a temperature comprised between 0 and 50° C., and at a pressure between 0 and 2000 psi.

The drospirenone coming from chromatography can possibly be subjected to crystallisation with a solvent selected for example from the group consisting of ethyl ether, isopropyl ether, methyl tert-butyl ether, ethyl acetate, isopropyl acetate, methyl acetate, dimethoxyethane, methanol, ethanol, isopropanol, methylene chloride, acetone, dimethylacetamide, dimethylformamide, and their mixtures; preferably the crystallisation solvent is isopropyl acetate.

The present process for the preparation of drospirenone as described above, has proved to be favourable because it enables the preparation of an intermediate, 7α-bromo-5,6β-epoxy-15β,16β-methylene-3β-pivaloyloxy-5β-androstan-17-one, useful for the synthesis of drospirenone, avoiding however the use of toxic solvents and reagents such as tetrachloromethane used in the process as given in EP 0 075 189. Moreover, the preparation of this brominated intermediate, while passing via the formation of a mesylated intermediate, does not involve an additional step in the process, in that the mesylate is not isolated but brominated directly.

The use of carcinogenic reagents is also avoided in the oxidation step g) which, in addition to not requiring carcinogenic reagents, is even more efficient than the oxidation with chromic anhydride described in EP 0 075 189. Moreover, by virtue of the fact that drospirenone is formed in a basic environment, a final product is obtained which lacks the impurities that drospirenone gives rise to in an acidic environment, as described in EP 0 918 791.

Finally, the purification process by gel chromatography enables the invert lactone fraction that is always present in the crude product and identified as ZK35096 in U.S. Pat. No. 6,121,465, to be completely eliminated. This purification process is applicable to and is useful for the purification of not only drospirenone prepared in accordance with the present process, but also products obtained with other processes in which the aforementioned invert lactone is present as an impurity.

The following examples are given as non-limiting illustrations of the present invention.

EXAMPLE 1

Preparation of 7α-bromo-5,6β-epoxy-15β,16β-methylene-3β-pivaloyloxy-5β-androstan-17-one 67.5 g of 5,6β-epoxy-7β-hydroxy-15β,16β-methylene-3β-pivaloyloxy-5β-androstan-17-one are dissolved in 205 ml of pyridine in a 2 litre flask, under nitrogen.

17.5 ml of mesyl chloride are added from a dropping funnel, at a temperature of 20/25° C.

The mixture is stirred for 1 hour at 20° C. to obtain a thick orange suspension.

The progress of the reaction is checked by TLC. At the end of the reaction 83.2 g of lithium bromide dissolved in 54 ml of water are added and the temperature is brought to 70/75° C. After 3 hours 8 g of lithium bromide dissolved in 50 ml of pyridine are further added.

At the end of the reaction (checked by TLC) the temperature is brought to 60° C. and 700 ml of water are added; it is left to cool to 15/20° C., stirring for 1 hour at this temperature.

The solid is filtered off and washed with 500 ml of water.

The solid is dried for 24 hours under reduced pressure at 45° C. to obtain 69.5 g of the compound of the title.

On the product thus obtained, purified by chromatographic means, $^1$H-NMR and mass spectroscopic analyses were carried out, and the following results were obtained:

$^1$H-NMR (300 MHz, CDCl$_3$): d (ppm) 0.92 (18-Me, s, 3H); 1.04 (19-Me, s, 3H); 1.08-1.16 (m, 1H); 1.16 (t-But, s, 9H); 1.18-1.28 (m, 1H); 1.36-1.60 (m, 8H); 1.62-1.68 (m, 1H); 1.72-1.76 (m, 1H); 1.84-1.96 (m, 3H); 2.04-2.16 (m, 3H); 3.46 (6-H, broad s, 1H); 4.73 (7-H, broad s, 1H); 4.76-4.84 (3-H, m, 1H). Mass by electron impact: m/z [376] and [378]=M$^+$-C(CH$_3$)$_3$—COOH; [297] and [299]=M$^+$-C(CH$_3$)$_3$—COOH—Br

EXAMPLE 2

Preparation of 5-hydroxy-15β,16β-methylene-3β-pivalovioxy-5β-androst-6-en-17-one 27 g of powdered zinc suspended in 91 ml of THF (tetrahydrofuran) are fed into a 1 litre flask, under nitrogen.

The suspension is heated to 40/45° C. and 19.9 ml of glacial acetic acid are slowly added dropwise, maintaining the temperature under 60° C. during the addition.

The suspension is stirred for 15 minutes at 40° C. after which a solution, preheated to 45° C., of 67.5 g of 7α-bromo-5,6β-epoxy-15β,16β-methylene-3β-pivaloyloxy-5β-androstan-17-one in 277 ml of THF, prepared as described in example 1, is added. The temperature is maintained at 48/50° C. during the addition.

The reaction mixture is stirred for 3 hours at 59/60° C.

At the end of the reaction (checked by TLC) it is cooled to 50° C. and the zinc is filtered off through dicalite; the filter is washed with 200 ml of THF.

The filtered solution is brought to pH 9 with 60 ml of triethylamine.

The solution is concentrated under reduced pressure at 50° C. to obtain about 180 g of a semisolid product which is taken up in 500 ml of a 5% acetic acid-water solution (pH=4 with a precipitate).

It is stirred for 1 hour at 10/15° C., the solid is filtered off and washed with 500 ml of water then dried under reduced pressure for 12 hours at 50° C. to obtain 57 g of crude product.

The crude product is refluxed for 1 hour in a mixture of t-butylmethylether=115 115 ml and ethyl acetate=114 ml (partial dissolution).

It is cooled for 1 hour at 0/5° C., the solid is filtered off and washed with t-butylmethylether and dried under reduced pressure for 1 hour at 60° C. 44.6 g of the title compound are obtained.

The analytical data obtained from a sample purified by chromatography correspond to those given in EP 0 075 189.

EXAMPLE 3

Preparation of 3β,5-dihydroxy-15β,16β-methylene-5β-androst-6-en-17-one 43 g of 5-hydroxy-15β,16β-methylene-3β-pivaloyloxy-5β-androst-6-en-17-one prepared as described above in Example 2, 430 ml of THF, 215 ml of methanol, 12.9 g of potassium hydroxide and 4.3 g of sodium perchlorate are fed into a 2 litre flask, under nitrogen at 20° C. The suspension is stirred at 20° C. for 3 hours.

At the end of the reaction (checked by TLC), the entirety is poured into 2 litres of water.

The suspension is brought to pH 7 with 20% sulfuric acid (about 25 ml) then stirred for 1 hour at 0/5° C. The solid is filtered off, washed with water and dried for 12 hours under reduced pressure at 50° C. to obtain 30.6 g of the title compound.

The analytical data obtained for a sample purified by chromatography correspond to those given in EP 0 075 189.

EXAMPLE 4

Preparation of 3β,5-dihydroxy-6β,7β;15β,16β-dimethylene-5β-androst-17-one 29 g of 3β,5-dihydroxy-15β,16β-methylene-5β-androst-6-en-17-one prepared as described above in Example 3 are fed into a 2 litre flask under nitrogen at 20° C. with 410 ml of THF.

0.6 g of copper (II) acetate hydrate are added and the mixture is stirred until a clear (green) solution appears.

37.9 g of finely powered zinc are added followed, after stirring for 15 minutes, by 1.7 ml of acetic acid.

The mixture is further agitated for 30 minutes at 20° C. then heated to 50° C., 32.3 ml of methylene bromide are then added and it is refluxed for 2 hours.

At the end of the reaction (checked by TLC) it is cooled to 20° C. and a mixture of acetic acid=26.8 ml in 450 ml water is added slowly while cooling.

The mixture is filtered through dicalite and the panel is washed with 600 ml toluene.

The phases are separated and the aqueous phase is extracted with 200 ml toluene.

The pooled organic phases are washed with 350 ml water.

The organic phase is dried over sodium sulfate, filtered and concentrated under reduced pressure at 60° C. until a solid is obtained.

The solid is taken up with 60 ml t-butylmethylether, filtered off and washed with a further 20 ml of t-butylmethylether.

The solid is dried for 12 hours under reduced pressure at 45° C. to obtain 25.5 g of the title compound.

The analytical data obtained from a sample purified by chromatography correspond to those given in EP 0 075 189.

EXAMPLE 5

Preparation of 17α-(3-hydroxy-1-propinyl)-6β,7β;15β,16β-dimethylene-5β-androstan-3β,5,17β-triol 24 g of 3β, 5-dihydroxy-6β,7β;15β,16β-dimethylene-5β-androst-17-one prepared as described above in Example 4 are fed into a 1 litre flask, under nitrogen at 20° C., with 480 ml THF.

The mixture is cooled to 0/5° C. and 72 g of potassium methylate are added (yellow suspension).

While maintaining the temperature at 0/5° C. 48 ml of propargyl alcohol diluted with 90 ml THF are added slowly (thick orange solution).

A further 150 ml of THF are added when the density of the solution renders stirring impossible. The solution is stirred for 12 hours at 0/5° C.

At the end of the reaction (checked by TLC) the very thick suspension is poured into 2 litres of water and ice (an orange solid precipitates) and the pH is adjusted to 7 with 62% sulfuric acid (about 60 ml).

The solid obtained is filtered off and washed with 300 ml of water.

The filtered liquid is extracted with 1.5 litres of isopropylacetate.

The organic phase is dried over sodium sulfate, filtered and concentrated under reduced pressure at 50° C. to obtain a solid.

The solid is filtered off from heptane and dried for 12 hours at 45° C. under reduced pressure to obtain 27.1 g of the title compound.

The analytical data obtained from a sample purified by chromatography correspond to those given in EP 0 075 189.

EXAMPLE 6

Preparation of 17α-(3-hydroxypropyl)-6β,7β;15β,16β-dimethylene-5β-androstan-3β,5,17β-triol A solution of 25.1 g of 17α-(3-hydroxy-1-propinyl)-6β,7β;15β,16β-dimethylene-5β-androstan-3β,5,17β-triol prepared as described above in Example 5, in 930 ml of a mixture prepared with 750 ml THF, 375 ml methanol and 1.5 ml of pyridine is fed into an autoclave.

5 g of 5% Pd/C catalyst are added and hydrogenation takes place at atmospheric pressure (20/25° C.) for 2 hours.

At the end of the reaction (checked by TLC) the suspension is filtered through dicalite and the filter is washed with methylene chloride.

The product is concentrated under reduced pressure at 50° C. to obtain 32 g of the title compound.

The crude title product contained small quantities of the two 6β,7β;15β,16β-dimethylene-3β,5β-dihydroxy-17α-pregn-21,17-carbolactols. It was nevertheless advantageously used for the subsequent reaction, without further purification.

A sample of the title product purified by chromatography gave the following results with $^1$H-NMR analysis:

$^1$H-NMR (300 MHz, CDCl$_3$): δ (ppm) 0.84 (18-Me, s, 3H); 0.88 (19-Me, s, 3H); 1.72 (s, —OH); 2.32-2.40 (m, —OH); 2.6(s, —OH); 3.38-3.40 (m, —OH); 3.64-3.76 (—CH$_2$OH, m, 2H); 4.0 (3-H, m, 1H).

The signals of the hydroxyl protons were identified by deuteration.

The crude reaction product used for the subsequent reaction also showed the following signals:

$^1$H-NMR (300 MHz, CDCl$_3$): δ (ppm) 5.50 (17-O—CHOH-21, t, 1H); 5.58 (17-O—CHOH-21, t, 1H).

EXAMPLE 7

Preparation of 6β,7β;15β,16β-dimethylene-5β-hydroxy-3-oxo-17α-pregn-21,17-carbolactol 10 g of 17α-(3-hydroxypropyl)-6β,7β; 15β,16β-dimethylene-5β-androstan-3β,5,17β-triol prepared as described above in Example 6 are dissolved in 250 ml of demethyl sulfoxide and 450 ml triethylamine, in a 2 litre flask under nitrogen.

30 g of pyridine-SO$_3$ complex are added in portions to the solution thus obtained while under stirring, maintaining the temperature at 20/25° C.

The mixture is stirred for 40 minutes at 20/25° C. then heated to 50/60° C. for a further 2 hours, checking the progress of the reaction by TLC.

At the end of the reaction 250 ml of water are added and the temperature brought to 0/5° C.

After 1 hour, the product is filtered off, washed with a 5% sodium hypochlorite solution and then with water and dried for 24 hours under reduced pressure at 45° C. obtaining finally 8.5 g of a product consisting of a mixture of the two possible 6β,7β;15β,16β-dimethylene-5β-hydroxy-3-oxo-17α-pregn-21,17-carbolactols, which is used directly in the next step without any purification.

$^1$H-NMR analysis carried out on the mixture highlights the appearance of two signals at 5.5 ppm and 5.58 ppm the sum of whose areas is equivalent to a proton (protons adjacent to oxygen of the carbolactol ring), and the disappearance of both the signal at 3.72 ppm (two protons of the free chain adjacent to oxygen) and the signal at 4 ppm (proton in position 3).

Mass by electron impact: m/z [386]=M$^+$
IR(KBr)=1707 cm$^{-1}$

EXAMPLE 8

Preparation of 6β,7β;15β,16β-dimethylene-3-oxo-17α-pregn-4-en-21,17-carbolactol 7.5 g of the mixture of the two 6β,7β;15β,16β-dimethylene-5β-hydroxy-3-oxo-17α-pregn-21,17-carbolactols obtained as aforedescribed in example 7 are dissolved in 300 ml of methanol and 750 mg of sodium methylate, in a 1 litre flask under nitrogen.

The solution thus obtained is left under agitation for 12 hours maintaining the temperature at 20/25° C., then 300 ml of water are added and the temperature is brought to 0/5° C.

After 1 hour the solid product which has formed is recovered by filtration, then the product is washed with water and dried for 24 hours under reduced pressure at 45° C., to obtain 6.5 g of a product shown to consist of a mixture of the two possible 6β,7β;15β,16β-dimethylene-3-oxo-17α-pregn-4-en-21,17-carbolactols.

Said mixture is then used directly in the subsequent step with no further purification.

In the $^1$H-NMR analysis of the mixture of carbolactols prepared as described above, the two signals at 5.5 ppm and 5.58 ppm are maintained (protons adjacent to oxygen of the carbolactol ring), with the appearance of a signal at 6 ppm (proton in position 4).

Mass by electron impact: m/z[368]=M$^{+IR(KBr)=}$1665,1595 cm$^{-1}$

EXAMPLE 9

Preparation of 6β,7β;15β,16β-dimethylene-3-oxo-17α-pregn-4-en-21,17-carbolactol 7.5 g of the mixture of the two 6β,7β;15β,16β-dimethylene-5β-hydroxy-3-oxo-17α-pregn-21,17-carbolactols obtained as described above in Example 7 are dissolved in 300 ml of pyridine and 50 ml of water in a 1 litre flask under nitrogen.

The solution thus obtained is left under stirring for 12 hours maintaining the temperature at 45/50° C., then 300 ml of water are added followed by extraction with ethyl acetate.

The organic phase containing the product is recovered, then washed with aqueous acetic acid and water until the pH is neutral. After drying over sodium sulfate and concentrating to dryness under reduced pressure, 6.4 g of a product, shown to consist of a mixture of the two possible 6β,7β;15β,16β-dimethylene-3-oxo-17α-pregn-4-en-21, 17-carbolactols, are obtained.

The analytical data of the product obtained correspond to those obtained from the sample of aforesaid Example 8.

The mixture obtained is used directly in the next step without additional purification.

EXAMPLE 10

Preparation of 6β,7β;15β,16β-dimethylene-3-oxo-17α-pregn-4-ene-21, 17-carbolactone (DRO-SPIRENONE)

10 g of a mixture of the two 6β,7β;15β,16β-dimethylene-3-oxo-17α-pregn-4-en-21,17-carbolactols obtained as described above in Example 9, previously dissolved in 280 ml of methylene chloride, are added to a 1 litre flask containing 280 ml of a 5% aqueous solution of sodium bicarbonate.

0.5 g of the 2,2,6,6-tetramethylpiperidine-1-oxyl radical and 16 g of calcium hypochlorite are added in portions under agitation at a temperature of 0/5° C.

The mixture is left under stirring for 1 hour while maintaining the temperature at 20/25° C., then the phases are separated and the solvent is removed under reduced pressure.

The crude reaction product is chromatographed over 100 g of silica gel, eluting with ethyl ether.

The product obtained from the chromatography is crystallised from isopropyl acetate.

After drying for 24 hours under reduced pressure at 45° C., 7.9 g of drospirenone are obtained whose analytical characteristics correspond to those given in the literature.

EXAMPLE 11

Preparation of 6β,7β;15β,16β-dimethylene-3-oxo-17α-pregn-4-ene-21,17-carbolactone (DRO-SPIRENONE)

10 g of a mixture of the two 6β,7β;15β,16β-dimethylene-5β-hydroxy-3-oxo-17α-pregn-21,17-carbolactols obtained as described above in Example 7, previously dissolved in 200 ml of methylene chloride, are added to a 1 litre flask containing 280 ml of a 5% aqueous solution of sodium bicarbonate.

0.5 g of the 2,2,6,6-tetramethylpiperidine-1-oxyl radical and 24 g of calcium hypochlorite are added in portions over a period of 3 hours under stirring at a temperature of 0/5° C.

100 ml of pyridine are added and the methylene chloride is distilled at room pressure.

When the distillation is finished the mixture is kept hot until the end of the reaction, then the solvent is concentrated under reduced pressure, and the crude reaction product is chromatographed over 250 g of silica gel eluting with ethyl ether.

The product obtained from the chromatography is, crystallised from isopropyl acetate.

After drying for 24 hours under reduced pressure at 45° C., 6.9 g of drospirenone are obtained whose analytical characteristics correspond to those given in the literature.

EXAMPLE 12

Preparation of 6β,7β;15β,16β-dimethylene-3-oxo-17α-pregn-4-ene-21,17-carbolactone (DRO-SPIRENONE)

5 g of the mixture of the two 6β,7β;15β,16β-dimethylene-3-oxo-17α-pregn-4-en-21,17-carbolactols obtained as described above in Example 8 are dissolved in 500 ml of toluene in a 1 litre flask under nitrogen. 50 ml of cyclohexanone are added to the solution thus obtained and then a total of 50 ml of overheads are distilled off.

The reaction mixture is then cooled to 80° C. and, after adding 10 g of potassium tert-butylate, refluxed for 2 hours.

At the end of the reaction the mixture is cooled to 40° C. and the solvent is removed under reduced pressure, to obtain a crude reaction product which is then chromatographed over 50 g of silica gel eluting with ethyl ether.

The product obtained from the chromatography is crystallised from isopropyl acetate.

After drying for 24 hours under reduced pressure at 45° C., 2.5 g of drospirenone are obtained whose analytical characteristics correspond to those reported in the literature.

EXAMPLE 13

Preparation of 6β,7β;15β,16β-dimethylene-3-oxo-17α-pregn-4-ene-21,17-carbolactone (DROSPIRENONE)

5 g of the mixture of the two 6β,7β;15β,16β-dimethylene-5β-hydroxy-3-oxo-17α-pregn-21,17-carbolactols obtained as described in the aforesaid Example 7 are dissolved in 500 ml of toluene in a 1 litre flask under nitrogen.

60 ml of methylisobutylketone are added and then a total of 50 ml of overheads are distilled off.

The reaction mixture is cooled to 80° C. and, after adding 12 g of potassium tert-butylate, refluxed for 5 hours.

At the end of the reaction, the mixture is cooled 40° C. and the solvent is removed under reduced pressure. The crude reaction product thus obtained is chromatographed over 50 g of silica gel eluting with ethyl ether.

The product obtained from the chromatography is crystallised from isopropyl acetate.

After drying for 24 hours under reduced pressure at 45° C., 1.2 g of drospirenone are obtained whose analytical characteristics correspond to those given in the literature.

EXAMPLE 14

Preparation of 6β,7β;15β,16β-dimethylene-3-oxo-17α-pregn-4-ene-21;17-carbolactone (DROSPIRENONE)

10 g of 17α-(3-hydroxy-1-propyl)-6β,7β;15β,16β-dimethylene-5β-androstan-3β,5,17β-triol prepared as described above in Example 6 are dissolved in 300 ml of toluene in a 2 litre flask under nitrogen.

60 ml of cyclohexanone are added then a total of 50 ml of overheads are distilled off.

The reaction mixture is cooled to 80° C., and after adding 10 g of potassium tert-butylate, refluxed for six hours.

Another 20 g of potassium tert-butylate are added in two portions and refluxed for a further 12 hours.

At the end of the reaction the mixture is cooled to 40° C. and the solvent is removed under reduced pressure by distilling excess oils with water.

The crude reaction product is chromatographed over 100 g of silica gel eluting with ethyl ether.

The product obtained from the chromatography is crystallised from isopropyl acetate.

After drying for 24 hours under reduced pressure at 45° C., 2,6 g of drospirenone are obtained whose analytical characteristics correspond to those given in the literature.

EXAMPLE 15

Preparation of 6β,7β;15β,16β-dimethylene-3-oxo-17α-pregn-4-ene-21,17-carbolactone (DROSPIRENONE)

10 g of 17α-(3-hydroxy-1-propyl)-6β,7β;15β,16β-dimethylene-5β-androstan-3β,5,17β-triol prepared as described above in Example 6 are dissolved in 400 ml of toluene in a 2 litre flask under nitrogen.

The mixture is heated to reflux, and 40 g of manganese dioxide are added in portions. The reaction mixture is cooled to 80° C., then maintained under stirring at this temperature for 16 hours.

At the end of the reaction the mixture is cooled, the solid is filtered off through dicalite and the solvent removed under reduced pressure.

The crude reaction product is chromatographed over 120 g of silica gel eluting with ethyl ether. The product obtained from the chromatography is crystallised from isopropyl acetate.

After drying for 24 hours under reduced pressure at 45° C., 3.3 g of drospirenone are obtained whose analytical characteristics correspond to those given in the literature.

EXAMPLE 16

Preparation of 6β,7β;15β,16β-dimethylene-3-oxo-17α-pregn-4-ene-21,17-carbolactone (DROSPIRENONE)

5 g of the mixture of the two 6β,7β;15β,16β-dimethylene-3-oxo-17α-pregn-4-en-21,17-carbolactols obtained as described above in Example 8 are dissolved in 280 ml of toluene in a 1 litre flask under nitrogen.

The mixture is heated to reflux and 20 g of manganese dioxide are added in portions.

The reaction mixture is cooled to 80° C. and maintained under stirring at this temperature for 16 hours.

At the end of the reaction the mixture is cooled, the solid is filtered off through dicalite and the solvent removed under reduced pressure.

The crude reaction product is chromatographed over 120 g of silica gel eluting with ethyl ether. The product obtained from the chromatography is crystallised from isopropyl acetate.

After drying for 24 hours under reduced pressure at 45° C., 2.5 g of drospirenone are obtained whose analytical characteristics correspond to those given in the literature.

EXAMPLE 17

Preparation of 6β,7β;15β,16β-dimethylene-3-oxo-17α-pregn-4-ene-21,17-carbolactone (DROSPIRENONE)

300 ml of acetonitrile, 10 g of N-methylmorpholine N-oxide, 13 g of 4 Angstrom molecular sieves, 500 mg of tetrapropylammonium perruthenate and 10 g of the mixture of the two 6β,7β;15β,16β-dimethylene-3-oxo-17α-pregn-4-en-21,17-carbolactols obtained as described above in Example 8 are fed into a 1 litre flask under nitrogen. This reaction mixture is maintained for 2 hours at 22° C. under agitation, monitoring the reaction with thin layer chromatography (TLC).

At the end of the reaction the mixture is filtered through dicalite, the filter is washed with acetonitrile, then the solvent is removed under reduced pressure. The solid is redissolved in methylene chloride and washed with water until the pH=7.

The phases are separated, the organic phase is dried over sodium sulfate, filtered off and the solvent removed under reduced pressure.

The crude reaction product is chromatographed over 120 g of silica gel eluting with ethyl ether. The product obtained from the chromatography is then crystallised from isopropyl acetate.

After drying for 24 hours under reduced pressure at 45° C., 5.1 g of drospirenone are obtained, whose analytical characteristics correspond to those given in the literature.

EXAMPLE 18

Preparation of 6β,7β;15β,16β-dimethylene-3-oxo-17α-pregn-4-ene-21,17-carbolactone (DROSPIRENONE)

In a 500 ml flask, placed on an alternate stirrer with speed of 100 rpm and run of 4 cm, containing 50 ml of a brothculture of *Acetobacter aceti* MIM ANTO, the mixture of the two 6β,7β;15β,16β-dimethylene-3-oxo-17α-pregn-4-en-21,17-carbolactols obtained as described above in Example 8 is added, so to attain a concentration of 2 g/l.

The flask is maintained under stirring for 24 hours at 28° C. checking the reaction progress by TLC (CH$_2$Cl$_2$/acetone 9/1).

Once the reaction is terminated, the brothculture is extracted with ethyl acetate, the organic phase is dehydrated on sodium sulphate and the solvent is eliminated at reduced pressure.

The raw product is chromatographed on 20 g of silica gel eluting with ethyl ether.

The product coming from chromatography is then crystallised using isopropyl acetate.

After drying for 24 hours at reduced pressure and 45° C., 65 mg of drospirenone are obtained, whose analytical characteristics coincide with what reported in literature.

The invention claimed is:

1. Process for the preparation of drospirenone comprising the following steps:

a) bromination of 5,6β-epoxy-7β-hydroxy-15β,16β-methylene-3β-pivaloyloxy-5β-androstan-17-one of formula (II), in position 7α, to obtain 7α-bromo-5,6β-epoxy-15β,16β-methylene-3β-pivaloyloxy-5β-androstan-17-one of formula (III)

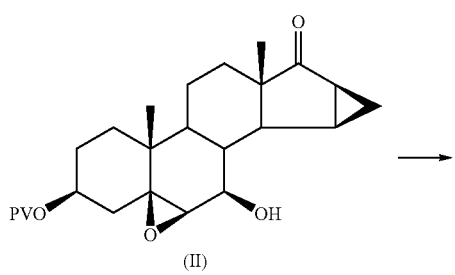

(II)

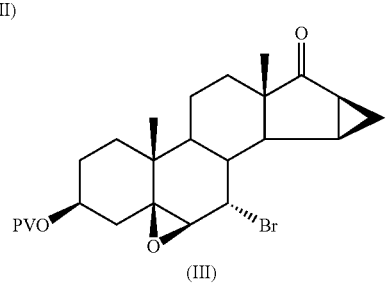

(III)

b) opening the epoxy ring of, and removing bromine from, 7α-bromo-5,6β-epoxy-15β,16β-methylene-3β-pivaloyloxy-5β-androstan-17-one of formula (III) to obtain 5-hydroxy-15β,16β-methylene-3β-pivaloyloxy-5β-androst-6-en-17-one of formula (IV)

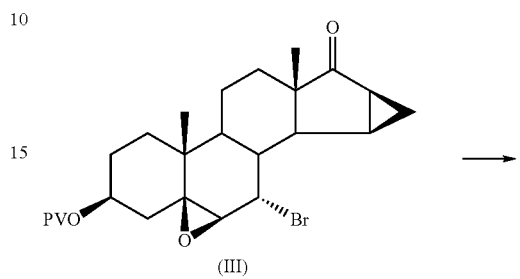

c) hydrolysis of the pivaloyl group of 5-hydroxy-15β,16β-methylene-3β-pivaloyloxy-5β-androst-6-en-17-one of formula (IV) to obtain 3β,5-dihydroxy-15β,16β-methylene-5β-androst-6-en-17-one of formula (V)

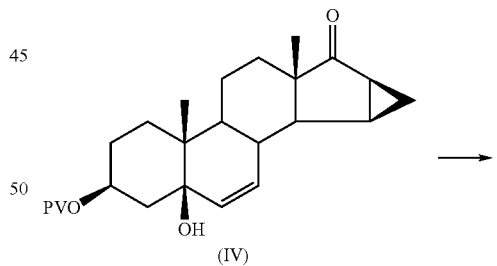

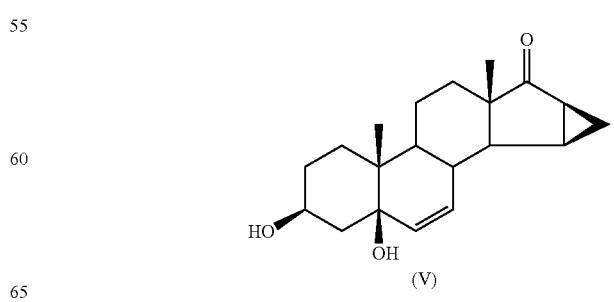

d) methylenation of 3β,5-dihydroxy-15β,16β-methylene-5β-androst-6-en-17-one of formula (V), at the Δ⁶ double bond, to obtain 3β,5-dihydroxy-6β,7β;15β,16β-dimethylene-5β-androst-17-one of formula (VI)

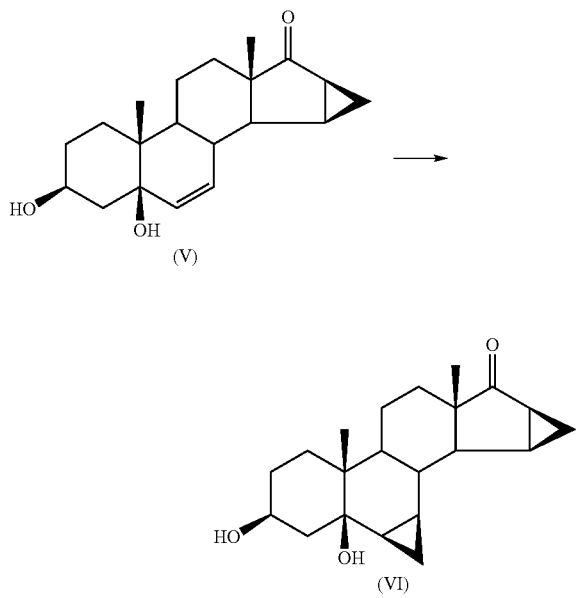

e) reacting 3β,5-dihydroxy-6β,7β; 15β,16β-dimethylene-5β-androst-17-one of formula (VI) with propargyl alcohol to obtain 17α-(3-hydroxy-1-propinyl)-6β,7β;15β,16β-dimethylene-5β-androstan-3β,5,17β-triol of formula (VII)

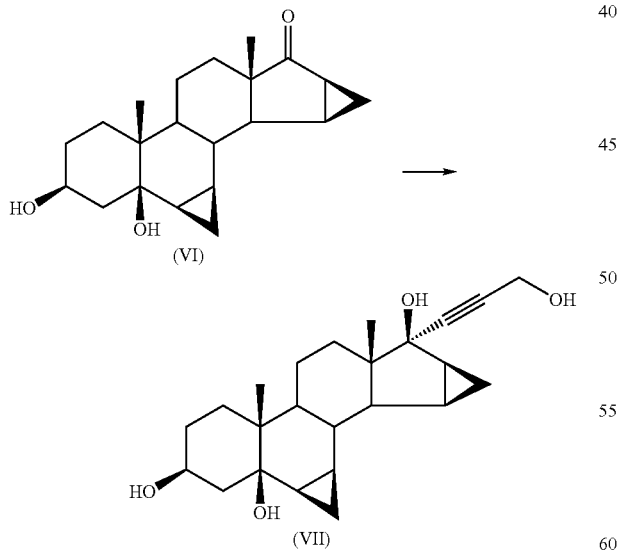

f) hydrogenating 17α-(3-hydroxy-1-propinyl)-6β,7β;15β,16β-dimethylene-5β-androstan-3β,5,17β-triol of formula (VII) to obtain 17α-(3-hydroxypropyl)-6β,7β;15β,16β-dimethylene-5β-androstan-3β,5,17β-triol of formula (VII)

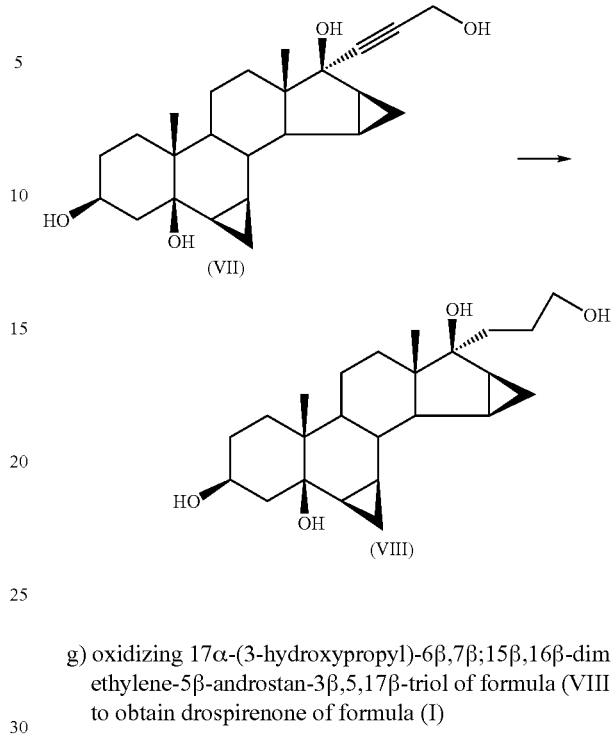

g) oxidizing 17α-(3-hydroxypropyl)-6β,7β;15β,16β-dimethylene-5β-androstan-3β,5,17β-triol of formula (VIII) to obtain drospirenone of formula (I)

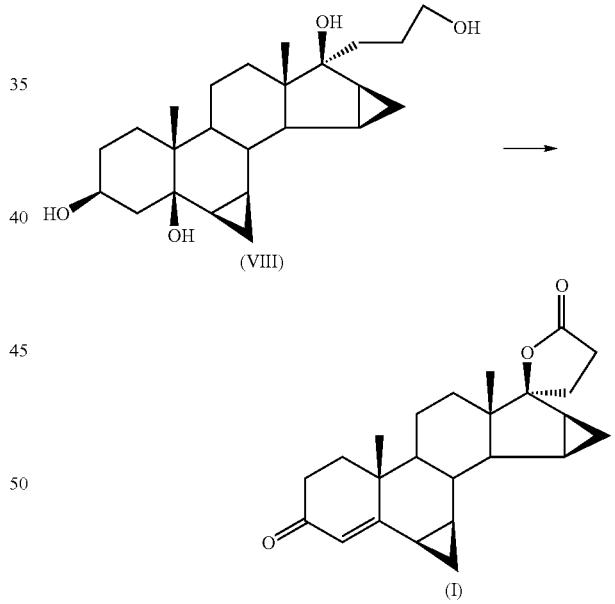

said process being characterised in that:
i) the 5,6β-epoxy-7β-hydroxy-15β,16β-methylene-3β-pivaloyloxy-5β-androstan-17-one of formula (II) in step a) is reacted with mesyl chloride to obtain the corresponding mesylate of formula (II-Ms), which is not isolated and from which 7α-bromo-5,6β-epoxy-15β,16β-methylene-3β-pivaloyloxy-5β-androstan-17-one of formula (III) is obtained by adding lithium bromide

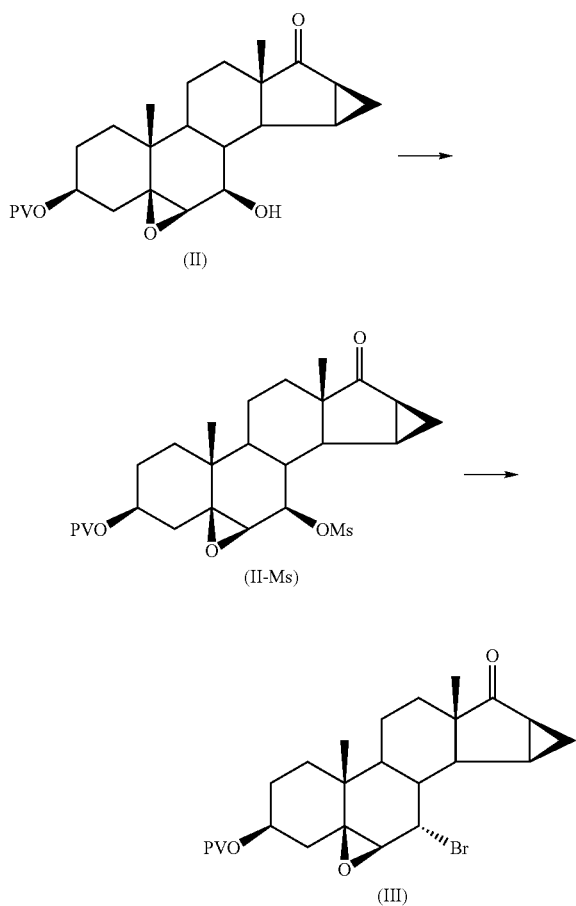

and
ii) said oxidation in step g) is carried out under such conditions that drospirenone forms under non-acidic pH conditions.

2. Process as claimed in claim 1, wherein said bromination reaction at step a) is undertaken by adding mesyl chloride and pyridine to the starting compound of formula (II) at room temperature with the formation of the corresponding mesylate of formula (II-Ms), then adding lithium bromide dissolved in water and bringing the temperature to values between 70 and 75° C.

3. Process according to claim 1, wherein said oxidation reaction at step g) is carried out by reacting 17α-(3-hydroxypropyl)-6β,7β;15β,16β-dimethylene-5β-androstan-3β,5,17β-triol of formula (VIII) with manganese oxide in toluene at a temperature between 40 and 110° C.

4. Process according to claim 1, wherein said oxidation at step g) is carried out by reacting 17α-(3-hydroxypropyl)-6β,7β;15β,16β-dimethylene-5β-androstan-3β,5,17β-triol of formula (VIII) with a base selected from aluminium isopropylate, potassium tert-butylate and sodium methylate in an organic solvent selected from toluene and xylene, in the presence of a ketone selected from methylisobutylketone, acetone and cyclohexanone, at a temperature between 80 and 110° C.

5. Process according to claim 1, wherein said oxidation at step g) is carried out by reacting 17α-(3-hydroxypropyl)-6β,7β;15β,16β-dimethylene-5β-androstan-3β,5,17β-triol of formula (VII) with a reagent selected from oxalyl chloride and pyridine-SO₃ in an organic solvent selected from dimethylsulfoxide and a dimethylsulfoxide-methylene chloride mixture, in the presence of triethylamine, to obtain 6β,7β;15β,16β-dimethylene-5β-hydroxy-3-oxo-17α-pregn-21,17-carbolactol in the form of an isomeric mixture of formula (IX)

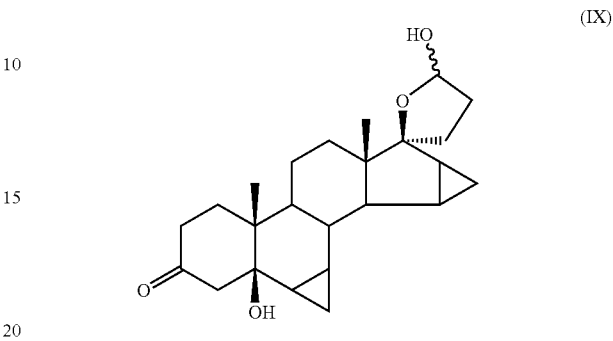

which is subjected to oxidation to obtain drospirenone of formula (I).

6. Process according to claim 5, wherein said oxidation of 6β,7β;15β,16β-dimethylene-5β-hydroxy-3-oxo-17α-pregn-21,17-carbolactol in the form of an isomeric mixture of formula (IX) to drospirenone of formula (I) is carried out with manganese dioxide in toluene at a temperature between 40 and 110° C.

7. Process according to claim 5, wherein said oxidation of 6β,7β;15β,16β-dimethylene-5β-hydroxy-3-oxo-17α-pregn-21,17-carbolactol in the form of an isomeric mixture of formula (IX) to drospirenone of formula (I) is carried out with a base selected from aluminium isopropylate, potassium tert-butylate and sodium methylate in an organic solvent selected from toluene and xylene, in the presence of a ketone selected from methylisobutylketone, acetone and cyclohexanone, at a temperature between 80 and 110° C.

8. Process according to claim 5, wherein said oxidation of 6β,7β;15β,16β-dimethylene-5β-hydroxy-3-oxo-17α-pregn-21,17-carbolactol in the form of an isomeric mixture of formula (IX) to drospirenone of formula (I) is carried out by reacting with sodium hypochlorite or calcium hypochlorite in an organic solvent selected from ethyl acetate, acetonitrile, toluene and methylene chloride at a temperature between 0 and 110° C. in the presence of an organic base selected from pyridine, 1,8-diazabicyclo[5.4.0]undec-7-ene and 1,5-diazabicyclo[4.3.0]non-5-ene, in the presence of a basic aqueous solution, and in the presence of a reagent selected from the 4-methoxy-2,2,6,6-tetramethylpiperidine-1-oxyl radical, the 4-(benzoyloxy)-2,2,6,6-tetramethylpiperidine-1-oxyl radical, the 4-hydroxy-2,2,6,6-tetramethylpiperidine-1-oxyl radical and the 2,2,6,6-tetramethylpiperidine-1-oxyl radical, said reaction being followed by distillation of the organic solvent.

9. Process according to claim 5, wherein said oxidation of 6β,7β;15β,16β-dimethylene-5β-hydroxy-3-oxo-17α-pregn-21,17-carbolactol in the form of an isomeric mixture of formula (IX) is carried out with a reagent selected from methylated sodium in methanol, potassium tert-butylate in tert-butanol, pyridine and a mixture of water and pyridine, at a temperature between 15 and 65° C. to obtain 6β,7β;15β,16β-dimethylene-3-oxo-17α-pregn-4-en-21,17-carbolactol in the form of an isomeric mixture of formula (X)

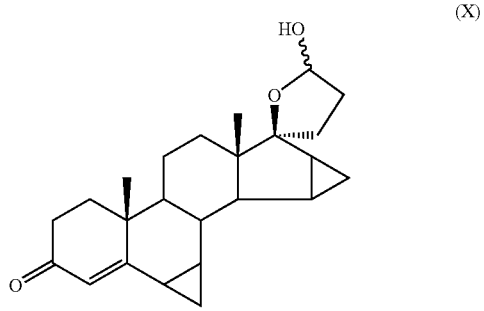

(X)

which is then subjected to oxidation to obtain drospirenone of formula (I).

10. Process according to claim 9, wherein said oxidation of 6β,7β;15β,16β-dimethylene-3-oxo-17α-pregn-4-en-21,17-carbolactol in the form of an isomeric mixture of formula (X) to drospirenone of formula (I) is carried out with manganese dioxide in toluene at a temperature between 40 and 110° C.

11. Process according to claim 9, wherein said oxidation of 6β,7β;15β,16β-dimethylene-3-oxo-17α-pregn-4-en-21,17-carbolactol in the form of an isomeric mixture of formula (X) to drospirenone of formula (I) is carried out with a base selected from aluminium isopropylate, potassium tert-butylate and sodium methylate in an organic solvent selected from toluene and xylene, in the presence of a ketone chosen from methylisobutylketone, acetone and cyclohexanone, at a temperature between 80 and 110° C.

12. Process according to claim 9, wherein said oxidation of 6β,7β;15β,16β-dimethylene-3-oxo-17α-pregn-4-en-21,17-carbolactol in the form of an isomeric mixture of formula (X) to drospirenone of formula (I) is carried out by reacting with sodium hypochlorite or calcium hypochlorite in an organic solvent selected from ethyl acetate, acetonitrile, toluene and methylene chloride at a temperature between 0 and 110° C. in the presence of an organic base selected from pyridine, 1,8-diazabicyclo[5.4.0]undec-7-ene and 1,5-diazabicyclo[4.3.0]non-5-ene, in the presence of a basic aqueous solution, and in the presence of a reagent selected from the 4-methoxy-2,2,6,6-tetramethylpiperidine-1-oxyl radical, the 4-(benzoyloxy)-2,2,6,6-tetramethylpiperidine-1-oxyl radical, the 4-hydroxy-2,2,6,6-tetramethylpiperidine-1-oxyl radical and the 2,2,6,6-tetramethylpiperidine-1-oxyl radical, said reaction being followed by distillation of the organic solvent.

13. Process according to claim 12, wherein said oxidation of 6β,7β;15β,16β-dimethylene-3-oxo-17α-pregn-4-en-21,17-carbolactol in the form of an isomeric mixture of formula (X) to drospirenone of formula (I) is carried out by reacting with calcium hypochlorite in methylene chloride at a temperature between 0 and 20° C., in the presence of 2,2,6,6-tetramethylpiperidine-1-oxyl radical in the presence of an aqueous solution of sodium bicarbonate.

14. Process according to claim 9, wherein said oxidation of 6β,7β;15β,16β-dimethylene-3-oxo-17α-pregn-4-en-21,17-carbolactol in the form of an isomeric mixture of formula (X) to drospirenone of formula (I) is carried out by reacting with a ruthenium salt in the presence of a base and a drying agent in an organic solvent selected from ethyl acetate, acetonitrile, toluene and methylene chloride, at a temperature between 0 and 110° C.

15. Process as claimed in claim 14, wherein said ruthenium salt is tetrapropylammonium perruthenate, said base is N-methylmorpholine N-oxide, said drying agent is molecular sieves, said organic solvent is acetonitrile, and said temperature is between 15 and 30° C.

16. Process according to claim 9, wherein said oxidation of 6β,7β;15β,16β-dimethylene-3-oxo-17α-pregn-4-en-21,17-carbolactol in the form of an isomeric mixture of formula (X) to drospirenone of formula (I) is carried out by microbiological route by adding said carbolactol to a brothculture of cells of acetic bacteria or to a suspension of the same bacteria cells obtained by centrifugation of the brothculture.

17. Process according to claim 16, wherein said acetic bacteria belong to the strain *Acetobacter aceti* MIM ANTO.

18. Process according to claim 16, wherein said oxidation is carried out by adding said carbolactol so that its concentration in the brothculture, or in the suspension of cells obtained by centrifugation of the brothculture, is 2 g/l.

19. Process as claimed in claim 1, further comprising a process for the purification of drospirenone of formula (I) comprising gel chromatography with an organic solvent as eluent.

20. Process as claimed in claim 19, wherein said gel is selected from the group consisting of silica gel, alumina, magnesium silicate and dextran, having a particle size distribution ranging from 5 to 200 μm, and said organic solvent is selected from the group consisting of ethyl ether, isopropyl ether, ethyl acetate, isopropyl acetate, methylene chloride, acetone, tetrahydrofuran, methanol, ethanol, isopropanol, hexane (n-hexane or a mixture of isomers), heptane (n-heptane or a mixture of isomers) and their mixtures.

21. Process as claimed in claim 19, wherein said gel is silica gel and said organic solvent is ethyl ether.

22. Process as claimed in claim 19, wherein the weight ratio of said gel to drospirenone (I) is between 5:1 and 25:1.

23. Process as claimed in claim 19, wherein the weight ratio of said gel to drospirenone (I) is equal to 10:1 and said organic solvent is pure ethyl ether.

24. Process as claimed in claim 19, wherein the drospirenone (I) is loaded after adsorption onto dry gel or dissolved in the elution solvent.

25. Process as claimed in claim 19, wherein in said gel chromatography column preparation and elution are carried out at a temperature between 0 and 50° C. and at a pressure between 0 and 2000 psi.

26. Process as claimed in claim 19, wherein said purification process of drospirenone (I) further comprises the crystallisation from a solvent of the product obtained from the gel chromatography.

27. Process as claimed in claim 26, wherein said crystallisation is carried out from a solvent selected from the group consisting of ethyl ether, isopropyl ether, methyl tertbutyl ether, ethyl acetate, isopropyl acetate, methyl acetate, dimethoxyethane, methanol, ethanol, isopropanol, methylene chloride, acetone, dimethylacetamide, dimethylformamide, and their mixtures.

28. Process as claimed in claim 27, wherein said solvent is isopropyl acetate.

29. Process tor the preparation of drospirenone, comprising a bromination reaction in position 7β of 5,6β-epoxy-7β-hydroxy-15β,16β-methylene-3β-pivaloyloxy-5β-androstan-17-one of formula (II) to obtain 7α-bromo-5,6β-epoxy-15β,16β-methylene-3β-pivaloyloxy-5β-androstan-17-one of formula (III), as described in claim 1.

30. Process for the preparation of drospirenone, comprising oxidation of 17α-(3-hydroxypropyl)-6β,7β,15β,16β-dimethylene-5β-androstan-3β,5,17β-triol of formula (VIII) to obtain drospirenone of formula (I), as described in claim 3.

31. Process for the preparation of drospirenone, comprising the oxidation of 6β,7β;15β,16β-dimethylene-3-oxo-17α-pregn-4-en-21,17-cabolactol in the form of an isomeric mixture of formula (X) to drospirenone of formula (I)

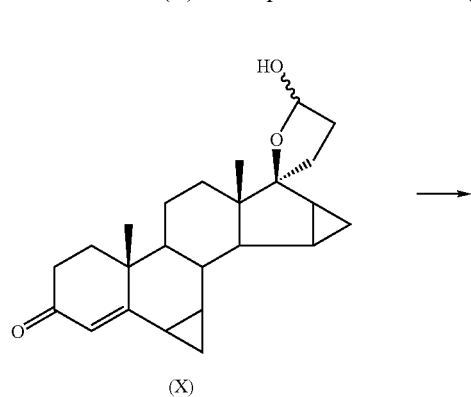

(X)

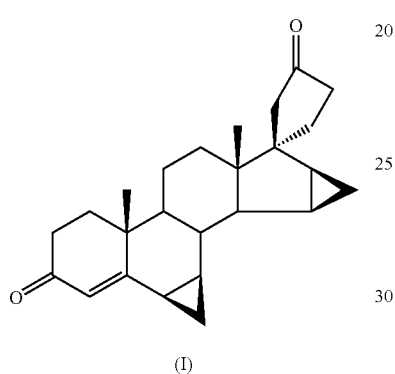

(I)

by microbiological route by adding said carbolactol to a brothculture of cells of acetic bacteria or to a suspension of the same bacteria cells obtained by centrifugation of the brothculture.

32. Process according to claim 31, wherein said acetic bacteria belong to the strain *Acetobacter aceti* MIM ANTO.

33. Process according to claim 31, wherein said oxidation is carried out by adding said carbolactol so that its concentration in the brothculture, or in the suspension of cells obtained by centrifugation of the brothculture, is 2 g/l.

34. The compound 6β,7β;15β,16β-dimethylene-5β-hydroxy-3-oxo-17α-pregn-21,17-carbolactol of formula (IX)

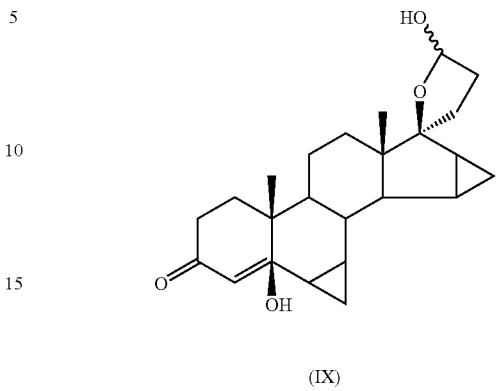

(IX)

in the ibrm of an isomeric mixture.

35. The compound 6β,7β,15β,16β-dimethylene-3-oxo-17α-pregn-4-en-21,17-cabolactol Of formula (X)

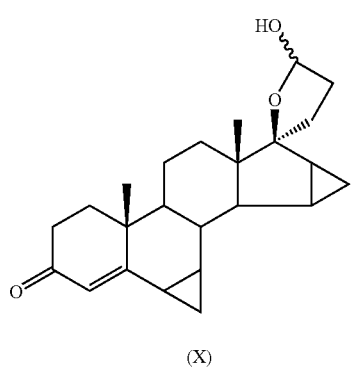

(X)

in the form of an isomeric mixture.

* * * * *